United States Patent
Sommer et al.

(10) Patent No.: US 7,108,993 B2
(45) Date of Patent: Sep. 19, 2006

(54) USE OF DUAL CONJUGATED LABELS IN THE ELIMINATION OF SERUM INTERFERENCE IN IMMUNOCHROMATOGRAPHIC ASSAYS

(75) Inventors: Ronald Sommer, Elkhart, IN (US); Lloyd Schulman, Osceola, IN (US); Daya C. Wijesuriya, Parkinson (AU)

(73) Assignee: Bayer Healthcare LLC, Tarrytown, NY (US)

( * ) Notice: Subject to any disclaimer, the term of this patent is extended or adjusted under 35 U.S.C. 154(b) by 734 days.

(21) Appl. No.: 10/198,890

(22) Filed: Jul. 19, 2002

(65) Prior Publication Data
US 2004/0014157 A1    Jan. 22, 2004

(51) Int. Cl.
*G01N 33/53* (2006.01)
*G01N 33/537* (2006.01)
*G01N 33/543* (2006.01)

(52) U.S. Cl. .......... 435/7.5; 436/518; 436/528; 436/810; 436/825; 435/7.94; 435/7.95; 435/287.8; 435/287.9; 435/970; 422/56; 422/57; 422/58; 422/60; 422/61

(58) Field of Classification Search ............ 436/518, 436/528, 810, 825; 435/7.93–7.95, 287.7, 435/287.8, 287.9, 970; 422/56–58, 60–61
See application file for complete search history.

(56) References Cited

U.S. PATENT DOCUMENTS

| | | | |
|---|---|---|---|
| 4,282,287 A | 8/1981 | Giese | |
| 4,313,734 A | 2/1982 | Leuvering | |
| 4,446,232 A | 5/1984 | Liotta | |
| 4,752,638 A | 6/1988 | Nowinski et al. | |
| 4,806,311 A | 2/1989 | Greenquist | |
| 4,868,108 A | 9/1989 | Bahar et al. | |
| 5,079,174 A | 1/1992 | Buck et al. | |
| 5,141,850 A * | 8/1992 | Cole et al. | 436/525 |
| 5,212,063 A | 5/1993 | Ofenloch-Hähnle et al. | |
| 5,234,812 A | 8/1993 | Buck et al. | |
| 5,296,347 A * | 3/1994 | LaMotte, III | 435/5 |
| 5,559,041 A * | 9/1996 | Kang et al. | 436/518 |
| 5,569,608 A * | 10/1996 | Sommer | 436/518 |
| 5,705,338 A * | 1/1998 | Piran et al. | 435/6 |
| 6,087,184 A * | 7/2000 | Magginetti et al. | 436/514 |
| 6,737,278 B1 * | 5/2004 | Carlsson et al. | 436/518 |
| 6,924,153 B1 * | 8/2005 | Boehringer et al. | 436/514 |

* cited by examiner

*Primary Examiner*—Bao-Thuy L. Nguyen

(57) ABSTRACT

A method and device for carrying out immunoassays in which non analyte specific binding of heterophilic antibodies to a labeled antibody in a capture region produces an incorrect measure of the amount of an analyte attached to the antibody. Immunoglobulin from the same animal source as the labeled antibody is added to the sample fluid to prevent non-specific binding of the heterophilic antibodies in the capture region. One part of specific binding pair is added to said antibody or its label capable of binding to a second part of the binding pair immobilized in a control region downstream of said capture region for trapping the portion of the labeled anti-body which is not bound to the analyte. Preferably said binding pair is biotin/avidin or fluoroscein/anti-fluoroscein.

9 Claims, 1 Drawing Sheet

USE OF DUAL CONJUGATED LABELS IN THE ELIMINATION OF SERUM INTERFERENCE IN IMMUNOCHROMATOGRAPHIC ASSAYS

BACKGROUND OF THE INVENTION

This invention relates generally to testing of biological fluids such as blood, urine, and the like, more particularly to immunoassays which employ antibodies to detect antigens.

Immunochromatographic strip formats have become increasingly popular for qualitative and semi-quantitative assays, particularly those which use visual detection schemes. This type of immunoassay involves the application of a liquid test sample suspected of containing an analyte to an application zone of an immuno-chromatographic strip. The presence of the analyte is typically indicated by a color which develops at a particular region of the strip. For example, pregnancy tests in which the analyte is human chronic gonadotropin (hCG).

Generally, a sample is brought into contact with an antibody to the analyte (i e, an anti-analyte antibody) which binds to the analyte, the antibody being labeled with a detectable moiety which, after separating the bound and free portions of the antibody, is used to indicate the amount of the analyte present. In order to collect the analyte bound to the antibody, a second anti-analyte antibody binding to a second epitope of the analyte may be immobilized on a test strip to capture the analyte bound to the first antibody. If the second anti-analyte antibody is not immobilized on a test strip, a pair of binding partners, typically a substance and its antibody, may be used to collect the second anti-analyte antibody. The first part of the binding pair is attached to the second anti-analyte antibody and the second part of the binding pair is immobilized at a specific location in a test strip to bind to the first part of the pair, thus immobilizing the analyte bound to the labeled first anti-analyte antibody so that it can be measured.

Usually, a test strip is comprised of a matrix material through which the test fluid, which may have the analyte suspended or dissolved therein, can flow by capillarity from the application zone to a detection zone where a detectable signal, or absence thereof, reveals the presence of the analyte. Typically, the strip will include means for immunospecifically binding the analyte to be detected with its specific binding partner which bears a detectable label. In one such scheme, as disclosed in U.S. Pat. No. 4,446,232, the strip contains an enzyme labeled, mobile binding partner for the analyte which is in a zone downstream from the sample application zone. If analyte is present in the test sample, it will combine with its labeled binding partner to form a complex which can flow along the strip to a detection zone which contains a substrate for the enzyme label capable of providing a colored response in the presence of the enzyme label. The strip also contains a zone in which analyte has been immobilized, so that the labeled binding partner which does not combine with the analyte, due to absence of analyte in the sample, will be captured and thereby prevented from reaching the detection zone. There have been published various modifications of this technique, all of which involve some specific binding system in which the presence or absence of analyte in the test sample is determined by the detection or lack thereof of labeled binding partner in the detection zone. In U.S. Pat. No. 4,868,108 there is disclosed a similar scheme with the addition of an immobilized capture reagent for the enzyme labeled binding partner in the detection zone to concentrate the enzyme label and enhance its ability to react with the enzyme substrate to thereby render the assay more sensitive.

Not all of the schemes for immunochromatography rely on an enzyme labeled binding partner/enzyme substrate to provide the signal for detection of the analyte. In U.S. Pat. No. 4,806,311 there is disclosed a multi zone test device for the specific binding assay determination of an analyte and an immobilized binding partner therefore together with a detection zone for receiving labeled reagent which migrates thereto from the reagent zone. The detection zone contains an immobilized form of a binding substance for the labeled reagent. The labeled reagent bears a chemical group having a detectable physical property, so that it does not require a chemical reaction with another substance. Exemplary of such groups are colored species, fluorescers, phosphorescent molecules, radioisotopes and electroactive moieties U.S. Pat. No. 4,313,734 describes the use of gold sols as labels for antibodies which are detectable without a chemical change.

The present invention relates to a method of overcoming interference with the results of immunoassays by non-specific binding of heterophilic antibodies in the sample to the labeled antibody. It was found that false positive results were occurring because an unbound labeled antibody was being retained in the detection region where it was expected that only those labeled antibodies which had bound to the target antigen (i e, the analyte) would be found. That is, the measurement of the amount of the bound antibody by using the label indicated the presence of the antigen, when none were present. Displacing the non-specific binding of the heterophilic anti-bodies was possible, but this created another difficulty, which was overcome by the present inventors, as will be seen in the description below.

SUMMARY OF THE INVENTION

The invention relates to a method for carrying out immunoassays and devices using the method. Interference caused by non-specific binding by a heterophilic antibody in the sample to a labeled antibody which is not attached to an analyte in the detection zone is overcome by adding non-analyte specific immunoglobulin from the same animal source as the labeled antibody. Recovery and measurement of the unbound labeled antibody is accomplished by attaching a moiety which is one part of a specific binding pair to the labeled antibody and immobilizing the second part of the binding pair to a region downstream of the detection zone. The labeled antibody bound to the analyte is immobilized in the detection (or capture) zone and the analyte-free labeled antibody is bound in the downstream region, making it possible to determine the ratio of the antibody bound to the analyte to the analyte-free antibody.

In one embodiment, the device includes three regions. The first region receives the sample and the added non-analyte specific immunoglobulin. A first anti-analyte antibody which carries a detectable label and the first part of a binding pair binds to analyte in the sample, either in the first region or before the sample is applied to the first region. The second region, e g the detection (or capture) zone, receives the sample from the first region and immobilizes the analyte bound to the antibody through a second anti-analyte antibody which is specific for a different epitope (i.e., a site for attachment of an antibody to an antigen) of the analyte. The amount of the analyte can be determined by measuring the detectable label in the second region. The third region receives the remaining sample from the second region and traps the portion of the labeled first antibody which was not bound to the analyte by the immobilized second part of the binding pair. The remaining sample then passes into an absorbent zone.

In an example of such an embodiment, the first anti-analyte antibody is goat polyclonal anti-analyte antibody and the second anti-analyte antibody is mouse mono clonal anti-analyte antibody. The label is colored latex particles. The immunoglobulin added to or with the sample is goat IgG. The first part of the binding pair preferably is biotin and the second part avidin.

In a second embodiment, the device also includes three regions, the first region receives the sample. The analyte in the sample is bound to a first anti-analyte antibody which carries a detectable label and the first part of a first binding pair and to a second anti-analyte antibody which binds the analyte at a different epitope to create a "sandwich" of analyte bound to two different antibodies. The second anti-analyte antibody is provided with the first part of a second binding pair, which is distinct from the first binding pair. The anti-analyte antibodies and the immunoglobulin may be placed in the first region or added to the sample before it is applied to the first region. The second region receives the sample from the first region and captures the second anti-analyte antibody with an immobilized second part of the second binding pair on the second anti-analyte antibody. The third region receives the remaining sample from the second region and traps the portion of the first anti-analyte antibody which did not bind to the analyte, using an immobilized second portion of the first specific binding pair on the first analyte antibody. The remaining sample then passes into an absorbent zone.

In an example of the second embodiment, the first anti-analyte antibody is goat polyclonal anti-analyte antibody and the second anti-analyte antibody is mouse mono clonal anti-analyte antibody. The label on the goat polyclonal anti-analyte antibody is colored latex particles. The first part of the first binding pair on the first anti-analyte antibody is biotin and the second part avidin. The first part of the second binding pair for the second anti-analyte antibody is fluorescein and the second part of the binding pair is anti-fluorescein. The immunoglobulin added to or with the sample is goat IgG.

In the method of the invention the first region either contains the necessary anti-analyte antibodies and immunoglobulin in a dry format for the first region may be free of the anti-analyte antibodies in which case the first region is dipped into a fluid mixture of the sample to which the antibodies and immunoglobulin have been added.

DESCRIPTION OF THE INVENTION

Typical Immunoassays

Figure 1:
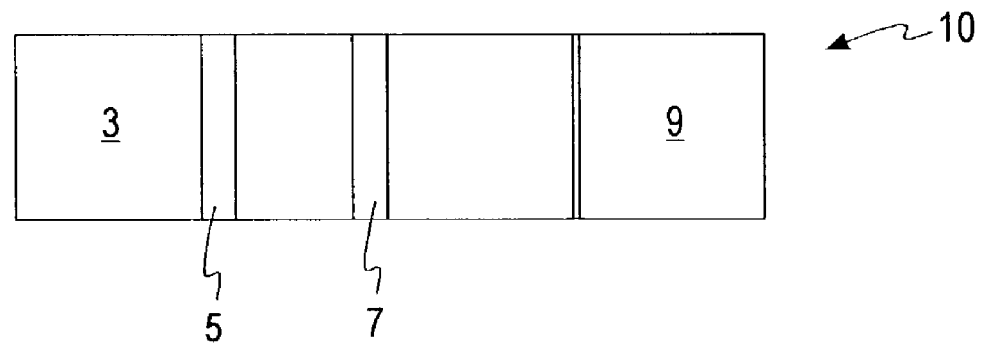
FIG. 1 illustrates one type of test strip used for immunoassays.

In this description of the invention, the terms "antigen" and "anti-body" may be used to refer respectively to a substance (e g. antigen) to which an animal responds by forming another substance (an antibody) which attaches to the first substance. These terms are commonly used in connection with respect to an animal's immune system. In an immunoassay an antigen, which can be considered an "analyte" (i e , the substance to be detected), is bound to an antibody which has been labeled. Antibodies are developed in animals in response to the introduction of antigens (analytes) to be detected in an immunoassay. Thus, the antibodies developed in response to analytes may be termed "anti-analyte antibodies", that is they will bind to the analyte when it is found in a sample fluid. Other antibodies, which may be termed "species specific anti-IgG antibodies" are antibodies which will bind to immunoglobulins (e.g. IgG) from a different animal. An example of this later type of antibody is one developed in rabbits in response to IgG from goats. The rabbit-derived antibody specific to IgG from goats will capture antibodies developed from goats and in some immunoassays is used to recover goat antibodies which are not bound to analyte found in a sample fluid.

In a typical immunoassay, the labeled antibody bound to an analyte is captured to separate it from the remaining labeled antibody which is not bound to analyte (the free portion). The amount of the label on the captured bound portion of the labeled antibody is measured to indicate the amount of analyte present in the sample. In order to obtain good quantitative accuracy, both the bound labeled antibody and the free labeled antibody should be trapped separately so that a ratio of the label associated with the bound antibody to the label associated with the unbound antibody can be obtained (see U.S. Pat. No. 5,569,608). Generally, the analyte bound to the labeled antibody is captured in a first region of a test strip (i.e the detection zone), with the antibody having no analyte attached passing with sample fluid to a second or control region where it is trapped and can be measured. This second region, which is important to obtaining accurate results, was found to present a problem which was solved by the present invention Most immunochromatographic strip tests are constructed so that the bound and free components of the immunoassay can be separated into two zones. With a "sandwich" assay this is usually accomplished by immobilizing an anti-analyte antibody (e.g., goat anti-analyte antibody) in a first zone and a species-specific anti-IgG antibody (e.g., rabbit anti-goat IgG antibody) in a second zone. The analyte in the sample binds to a non-immobilized labeled anti-analyte antibody and the complex is subsequently bound to the immobilized anti-analyte antibody in the first zone, creating a "sandwich" i.e., a single analyte (e.g., antigen) bound to two antibodies. The antibody of the second zone is specific for the IgG of the species in which the labeled anti-analyte antibody was raised, and will bind the free labeled anti-analyte antibody. With this scheme, the labeled anti-analyte antibody that does not bind to analyte (i.e the free component of the immunoassay) will not bind in the first zone, but is bound in the second zone.

Strips using this separation format are shown in FIG. 1. The labeled anti-analyte antibody is either placed on zone (3) or it may be used as which the sample containing the analyte is added. After the proper amount of time has been allowed for complex to form between the labeled antibody and the analyte, the zone 3 of the strip is placed in the sample/labeled antibody mixture to a depth such that the liquid will not contact either zone of immobilized antibodies (5 and 7). If the labeled antibody is applied to and dried on zone 3 and the sample is applied to zone 3, the components of the mixture will then flow along the strip until they contact the first zone (5) in which has been immobilized another anti-analyte antibody, which is specific for a different epitope of the analyte than binds to the first anti-analyte antibody. The first anti-analyte antibody that has complexed with analyte will be bound in zone 5 by the second anti-analyte antibody. The remaining components of the mixture will flow along the strip and contact the immobilized species-specific anti-IgG in the second zone (7) where the analyte-free antibody will be bound. This second band is sometimes referred to as a control band because one of the functions that it serves is to provide a detectable signal to inform the user that the assay has operated correctly. However, it captures all of the unbound conjugate and is valuable for use in quantitative calculations. The absorbent material in the last zone (9) serves as a fluid sink and will pull the entire sample through the strip in order to maximize the amount of antibody bound in zones 3 and 5.

Another closely related format can also be described in terms of FIG. 1. In this format the labeled first anti-analyte antibody is identical to that described above. However, instead of immobilizing the second anti-analyte antibody in zone 5, it is attached to a different moiety that produces no detectable signal, but for which there is available a specific binding partner. This is called a "binding pair". In this system the specific binding partner for that different moiety is immobilized in the first band (5) and the second band (7) is identical to that described above. For example, when fluorescein is used as the moiety attached to the second anti-analyte antibody, then mouse mono clonal anti-fluorescein antibody is immobilized in zone (5). The first detectably labeled anti-analyte antibody and the second non-detectably labeled anti-analyte antibody can be used in this format as a liquid suspension to which the sample containing the analyte is added. After the proper amount of time has been allowed for a "sandwich" complex to form between the two antibodies and the analyte, the lower section (3) of the strip in FIG. 1 is placed in the sample/labeled antibodies mixture to a depth such that the liquid will not contact either zone (5) or zone (7) of immobilized antibodies and the strip is developed in the identical manner as described above. Alternatively, the two anti-analyte conjugates can be deposited and dried in zone 3 and the sample applied to zone 3. With this format all of the second anti-analyte antibody and the analyte bound in a sandwich between the two antibodies binds in the first zone (5) and the analyte-free first labeled anti-analyte antibody is bound in the second zone (7). This latter format allows more time for the entire sandwich formation to take place The Problem It was discovered in a test for prostate specific antigen (PSA) prepared by the method of the latter type of assay using goat polyclonal anti-PSA antibody labeled with blue latex particles and mouse mono clonal anti-PSA antibody with fluoroscein attached gave false positive results for some serum samples. The analyte sandwich was trapped by anti-fluorescein anti-body immobilized in the first band (5). Approximately one third of the serum from normal female donors (which should not contain PSA) caused a positive indication in the first zone (5) of the strip. It is believed that heterophilic antibodies in the sample were non-specifically bound to the labeled anti-PSA antibody. In effect, the heterophilic antibodies caused the labeled anti-PSA antibodies to be trapped and read as containing PSA, although none was present. The mechanism which causes this interference is unknown, but one possible mechanism involves agglutination of the labeled particles with resultant steric hindrance of the agglutinate causing them to be unable to flow through the immobilized anti-fluorescein antibody zone. It was found that this problem could be resolved by adding normal goat (that is, from goats not immunized with PSA) IgG to the test sample before its application to the test strip However, since the rabbit-derived anti-goat IgG used in the second band (7) bound goat IgG from all sources, the normal goat IgG added to the test sample to eliminate the interference resulted in the signal from zone 7 being lost. In order to obtain the best quantitation, it is necessary to have all of the labeled conjugates (both bound and free) bind in the appropriate band, so that the amounts of both may be measured and used in calculations as described in U.S. Pat. No. 5,569,608. Our invention prevents the disappearance of the signal from this second band while still removing the interference from interfering serum samples.

The problem was solved by attaching biotin as a second affinity binding ligand to the colored latex particle which already had the goat anti-PSA antibody attached to it and immobilizing its affinity binding partner (avidin) in the collection zone 7. That is, a second binding pair was biotin/avidin. The second affinity binding ligand could also be, for example, glucose oxidase, dinitrophenol, digoxin or maltose binding protein. Any affinity ligand which binds with its affinity binding partner independently from the analyte being sought and is present in negligible concentrations in the samples containing the analyte is suitable for use in the present invention. For the affinity ligands mentioned above, their affinity binding partners would be, respectively, anti-glucose oxidase, anti-dinitrophenol, anti-digoxin, or anti-maltose binding protein.

In the case of biotin as the affinity ligand, the particle coupling can be achieved either by biotinylation of the analyte specific antibody followed by coupling to the carrier particle or by coupling of biotin attached to an inert protein, such as. BSA-biotin, which is coupled along with the analyte specific antibody to the carrier particle. The carrier particle is usually colored and serves as a detectable label. This method could also be used with non-particulate labels such as enzyme labels or other soluble detectable labels.

Figure 2:
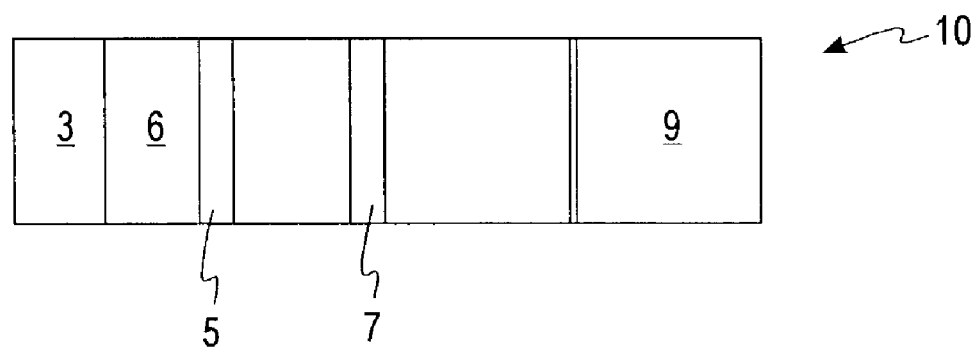
FIG. 2 illustrates a second type of test strip used for immunoassays.

The system described above uses a liquid phase sample/labeled anti-analyte antibody mixture. However, the same immunochromatographic assays can be performed with a completely dry phase system in which the labeled anti-analyte conjugates are dried into the solid phase material without immobilizing them and portions of this material placed in area 6 between area 3 and area 5 of FIG. 2. In this case the sample can be added to the material containing the labeled anti-analyte conjugates or to a blank area 3 which precedes it. The development of the assay then proceeds as described above.

The invention is illustrated in the following examples, using a test for prostate specific antigen (PSA).

EXAMPLE I

Two methods of adding biotin and blue latex particles to an antibody were demonstrated, as follows 1. Biotinylation of anti-PSA goat IgG Anti-PSA IgG (Bayer) (2 mg) was buffer exchanged into 0 1 M sodium phosphate (pH 7.0). The resulting solution was then concentrated to 0.5–1.0 mL. Biotin-NHS (N-hydroxysuccinimidyl biotin) (20 mg) (Pierce) was dissolved in 0.2 mL of water and 70 µL of this solution was added to the antibody solution and incubated for 1 hour @ 30° C. The solution was passed through a column of. Sephadex G-25 resin and past a UV detector which detected the coupled material (conjugate). A dot blot assay was performed in which 2 µL of the conjugate was applied to a piece of nitrocellulose along with native anti-PSA IgG in a different spot. The nitrocellulose was dried at 85° C. for ½ hour and then blocked with 1% (w/v) casein blocker for 15 minutes followed by 3 washes with PBS (Sigma) to remove unbound material. A 1 μg/mL solution of. Avidin-HRP (Avidin-Horse Radish Peroxidase) (2 μL) w followed by 3 washes with PBS. The membranes were dried at 85° C. for ½ hour whereupon a drop of 1-step TMB (tetramethyl benzidine) solution was applied to each spot to detect HRP. It was observed that the coupled material turned blue whereas the uncoupled IgG remained colorless. The biotinylated antibody was then coupled to blue latex as follows:

Dark blue latex, 1 mL of a 10% (w/v) in water (Bang Laboratories, lot # CAB 540, 310 nm diameter) was centrifuged @ (12000 RPM for 15 minutes. The supernatant was removed and the latex particles were re-suspended in 10 mL of 0.1 M sodium carbonate, pH 9.6. The latex suspension was again centrifuged @ 12000 RPM and the washing step was repeated three more times whereupon the latex particles were re-suspended in 1.0 mL of 0.02 M $KH_2PO_4$ mixture was stirred for 90 minutes at room temperature, centrifuged and re-suspended in 10 mL of 017 M NaCl. The suspension was again centrifuged and the supernatant decanted whereupon the latex pellet was resuspended in 125 mL of 50 mM borate (pH 8.5) and mixed well. Biotinylated anti-PSA polyclonal goat antibody (0.325 mg in 1 mL of PBS) was added dropwise and stirring was continued for 90 minutes at room temperature. One molar ethanolamine (10 μL) was added followed by an additional 30 minutes of stirring. Bovine serum albumin ("BSA") (5% w/v-100 μL) was added followed by another 30 minutes of stirring. The latex mixture was centrifuged and re-suspended in 10 mL of resuspension buffer (2 mg/mL BSA, 0.05% (w/v) Triton X-100 in 01 M glycine-0.17 M NaCl buffer, pH 82 containing 0.2% (w/v) sodium azide). The mixture was again centrifuged and the supernatant removed whereupon the latex was re-suspended in 75 mL resuspension buffer and the latex solution was probe sonicated for 30 seconds. The antibody coupled latex was stored @ 4° C.

2. Coupling of Biotin Attached to an Inert Protein (BSA-biotin) along with the Analyte Specific Antibody to the Carrier Particle 1.0 mL of Carboxy Dark Blue Latex particles, were washed 3 times with 10 mL of 0.1 M sodium carbonate buffer @ pH 9.6. The latex was suspended in 1 mL of 0.02 M $KH_2PO_4$ and was then activated by adding 2 mL of a 2% (w/v) EDAC solution and incubated for 90 minutes at room temperature. The latex was washed with 0.17 M NaCl and re-suspended with 1.25 mL of 50 mM borate buffer (pH 8.5).

Anti-PSA goat IgG (2 mg) was adjusted to a final volume of 1 25 mL with 50 mM borate (pH 8 5) in a test tube and 150 μg of. BSA-biotin added to the solution which was then vortexed. This solution was then added dropwise to the 1.25 mL of activated latex solution and stirred for 90 minutes at room temperature. 10 μL of 1 M ethanolamine was added followed by stirring for 30 minutes to quench the reaction and the addition of 100 μL of 5% (w/v). BSA with an additional 30 minutes of stirring to block any unbound binding sites. The coupled latex solution was washed 2 times with resuspension buffer (2 mg/mL. BSA, 0.05% (w/v). Triton X-100, 0 17 M glycine, 0 17 M NaCl, 0 2% azide (pH 8 2) and stored in 15 mL of the resuspension buffer @ 4° C. The final suspension was probe sonicated for 30 seconds.

3. Biotin-free latex-labeled anti-PSA antibody

For comparison with the labeled antibodies described under 1 and 2 above, a biotin-free antibody was prepared. 1.0 mL of Carboxy Dark Blue Latex particles were washed 3 times with 10 mL of 0.1 M carbonate buffer @ pH 9.6. The latex was suspended in 1 mL of 0.02 M $KH_2PO_4$ and then activated by adding 2 mL of a 2% (w/v) EDAC solution and incubated for 90 minutes at room temperature. The latex was washed with 0 17 M NaCl and re-suspended with 1 25 mL of 50 mM borate buffer (pH 8 5).

Anti-PSA goat IgG (2 mg) was adjusted to a final volume of 1 25 mL with 50 mM borate (pH 8 5) in a test tube. This solution was added dropwise to the 1 25 mL of activated latex solution and stirred for 90 minutes at room temperature 10 μL of 1M ethanolamine was added, followed by stirring for 30 minutes to quench the reaction and the addition of 100 μL of 5% (w/v). BSA with an additional 30 minutes of stirring to block any unbound binding sites. The coupled latex solution was washed with resuspension buffer (2 mg/mL. BSA, 0.05% (w/v). Triton X-100, 0 17 M glycine, 0 17 M NaCl, 0 2% azide (pH 8 2) and stored in 15 mL of the resuspension buffer @ 4° C. The final suspension was probe sonicated for 30 seconds.

4 Use of Latex Conjugates of 1, 2 and 3 in. Assay Mixtures

Casein [456 μL, 1% (w/v)] was mixed with 60 μl of 10% (w/v) Triton X-100 and 60 μL of coupled latex solution; the mixture was sonicated for 4 seconds. Anti-PSA mono clonal mouse antibody with fluorescein attached (Bayer) was then added and vortexed. This mixture, when added to a serum sample is capable of forming a "sandwich" in which PSA is attached to both the latex labeled goat-derived anti-PSA antibody and the mouse-derived anti-PSA antibody with fluorescein attached.

Nitrocellulose Membrane Preparation

Anti-fluorescein labeled mouse mono clonal antibody and rabbit-derived anti-goat IgG anti-body were striped as separate bands onto nitrocellulose using an IVEK striper with a table speed of 30 mm/sec, dispensing rate=1.2 μL/cm, anti-FITC concentration=1.5 mg/mL, rabbit anti-goat IgG concentration=1 1 mg/mL. In the first set of tests to be described below the latex conjugate of 3 was used. This conjugate contained no biotin, to illustrate the problem with non-specific binding. In the second set of tests the latex conjugate of 2 was used and NeutraAvidin (Pierce) concentration=1 mg/mL replaced the rabbit anti-goat IgG (i.e., striped on the nitrocellulose) to illustrate an embodiment of the invention. The nitrocellulose (25 mm wide) was then mounted at the bottom edge of a 108 mm wide polystyrene sheet material and a 32 mm strip of desiccant paper (Drikette from Multisorb) that overlapped the striped nitrocellulose by 1 mm was mounted on the polystyrene 7.5 mm wide strips were slit perpendicular to the bottom edge Assay Latex assay mixtures (30 μL) of preparations 2 (Table 2) or 3 (Table 1) were separately mixed with 15 μL of blood serum sample in a small test tube. The nitrocellulose strip was added and allowed to develop vertically for 10 minutes. The response of each band was measured on a reflectance photometer configured to detect narrow bands Data A Latex conjugated only with goat anti-PSA antibody (preparation 3) was used in the liquid phase sample/anti-analyte conjugate format along with the strip construction shown in the FIG. 1 in which the collection band (7) was immobilized rabbit antigoat IgG antibody. Serums containing no PSA and that either did or did not interfere with the binding in the capture band were used as samples. The non-interfering serum was used both with and without spiking to a PSA concentration of 15.7 ng/mL with. ACT-PSA (Scripps Laboratories). Additionally, each of the samples was assayed with and without 1.45 mg/mL of normal goat IgG in the assay mixture. The resulting data are set out in Table 1.

TABLE 1

| Serum Type | ACT-PSA (ng/mL) | Normal Goat IgG | Peak Height Reflectance (% R) (n = 3) | |
|---|---|---|---|---|
| | | | Capture Band | Collection Band |
| Interfering | 0 | absent | 6.1 ± 0.6 | 7.7 ± 0.4 |
| Interfering | 0 | present | 0 | 0 |
| Non-interfering | 0 | absent | 0 | 7.5 ± 0.4 |
| Non-interfering | 0 | present | 0 | 0 |
| Non-interfering | 15.7 | absent | 8.5 ± 0.4 | 5.5 ± 0.62 |
| Non-interfering | 15.7 | present | 10.0 ± 0.6 | 0 |

The data of Table 1 show high reflectance in the capture band in the absence of PSA when an interfering serum is used as a sample, thus giving a false positive reading even though the serum contained no PSA. The interference is eliminated by the addition of normal goat IgG, but the reflectance in the collection band is also lost, indicating that the unbound goat anti-PSA antibody was not being recovered in the collection band. When non-interfering serum was tested it can be seen that the capture band, as expected, did not show bound PSA, but the collection band did recover unbound goat anti-PSA antibody. However, adding goat IgG prevented its collection. Adding ACT-PSA provided a normal response in both the capture and collection bands, but adding goat IgG blocked recovery of unbound antibodies. In order to prevent interfering non-specific binding it was concluded that adding the goat IgG to the serum sample was important However, the ability to measure the unbound goat-derived anti-PSA antibodies was lost.

B Latex conjugated with both anti-PSA antibody and biotinylated BSA (preparation 2) was used in the liquid phase sample/labeled anti-analyte conjugate formats along with the strip construction shown in FIG. 1 in which the collection band (7) was immobilized neutrAvidin. Serums that either did or did not interfere with the binding in the capture band were used as samples again, and the non-interfering serum as used both with and without spiking to a PSA concentration of 15.7 ng/mL with ACT-PSA as before. Each of the samples was assayed with and goat IgG as in Table 1. The data from these experiments are shown in Table 2.

TABLE 2

| Serum Type | ACT-PSA (ng/mL) | Normal Goat IgG | Peak Height Reflectance (% R) (n = 3) | |
|---|---|---|---|---|
| | | | Capture Band | Collection Band |
| Interfering | 0 | absent | 16.1 ± 1.2 | 32.6 ± 0.3 |
| Interfering | 0 | present | 0 | 36.1 ± 0.4 |
| Non-interfering | 0 | absent | 1.9 ± 0.2 | 36.7 ± 0.4 |
| Non-interfering | 0 | present | 1.9 ± 0.2 | 37.2 ± 0.7 |
| Non-interfering | 15.7 | absent | 16.8 ± 2.7 | 33.8 ± 0.8 |
| Non-interfering | 15.7 | present | 18.5 ± 0.1 | 32.4 ± 0.6 |

The data of Table 2 demonstrate high reflectance in the capture band in the absence of PSA when an interfering serum is used as the sample. The interference is eliminated by the addition of normal goat IgG, and, unlike the case in which the latex is conjugated with only goat anti-PSA (that is, biotin was absent), the reflectance in the collection band remained constant. The interference is substantial in the absence of added goat IgG, providing a clearly false positive. When goat IgG is added, the interference is removed, but the collection band containing NeutrAvidin is effective, while in Table 1 the collection band gave no reading. The non-interfering serum gave a small reading for PSA captured, but this result is considered to be a low level background signal. However, when. ACT-PSA was added the effect of adding goat IgG was not significant. Thus, labeling the latex-labeled anti-PSA goat antibody with biotin, made it possible to bind the antibodies which are not bound to PSA in the collection band and permitting calculation of the ratio of antibodies bound to PSA in the sample to unbound antibodies.

Example 2

Preparation #2 from Example 1 is repeated to make a latex-labeled anti-PSA goat antibody, the latex also being coupled to biotin-BSA. This suspension is mixed with casein and mixed with a serum sample as described in Example 1.

Instead of adding an anti-PSA mono clonal mouse antibody labeled with fluorescein to the serum sample to create a "sandwich" prior to immersing the test strip, the anti-PSA mouse antibody is placed on the test strip as a first band. The "sandwich" is then formed when the PSA analyte is bound to the latex-labeled anti-PSA goat antibody and to the anti-PSA mouse antibody in the first, or capture band.

The test strip is prepared as in Example 1 except that the first band contains immobilized anti-PSA mouse antibody. As in Example 1, the second or collection band contains NeutrAvidin.

When the test strip is partially immersed in a sample to which latex-labeled anti-PSA goat antibody has been added, it is found that interfe removed by adding goat IgG, but the collection band can recover unbound latex-labeled anti-PSA goat anti-body by including NeutrAvidin in the collection band.

Example 3

The procedure of Example 2 is repeated, except that the latex-labeled anti-PSA goat antibody and goat IgG are dried on the test strip in a form that can be resuspended before the first band containing immobilized anti-PSA mono clonal mouse antibody. When the strip is partially immersed in the serum sample, reaction between the PSA in the sample and the anti-PSA goat antibody occurs on the strip. The sample then migrates through the capture band where the bound anti-PSA goat antibody labeled with latex particles is also bound to the anti-PSA mouse antibody. Thereafter the sample migrates to the second collection band where the remaining unbound anti-PSA goat antibody labeled with latex particles is recovered by biotin on the latex binding to NeutrAvidin immobilized on the second band.

What is claimed is:

1. A device for determining the amount of an analyte in a fluid test sample containing heterophilic antibodies which non-specifically bind to antibodies used to capture and immobilize labeled antibodies, said device comprising a test matrix having:
   (a) a first region for receiving said sample, said first region containing a first anti-analyte antibody conjugated with a detectable label and one part of a specific binding pair; said first region further containing an amount of an immunoglobulin from the same animal source as said first anti-analyte antibody sufficient to prevent non-specific binding of said heterophilic antibodies in the second region;

(b) a second region for receiving said sample from said first region and capturing and immobilizing said first anti-analyte antibody bound to an analyte in said sample, said second region containing an immobilized second anti-analyte antibody which is specific for a different epitope of said analyte than said first anti-analyte antibody;

(c) a third region for receiving said sample from said second region and trapping the portion of said first anti-analyte antibody not bound to said analyte, said third region containing an immobilized second part of said specific binding pair of said first region; and (d) an absorbent region for receiving said sample from said third region.

2. The device of claim 1 wherein said first anti-analyte antibody is goat polyclonal anti-analyte and said second anti-analyte antibody is mouse mono clonal anti-analyte.

3. The device of claim 1 wherein said label is selected from the group consisting of colored latex particles, metal sols, and enzymes.

4. The device of claim 1 wherein said immunoglobulin is IgG.

5. The device of claim 1 wherein each part of said binding pair has a negligible concentration in said sample.

6. The device of claim 5 wherein said binding pair is selected from the group consisting of fluoroscein/anti-fluoroscein, biotin/avidin, glucose oxidase/anti-glucose oxidase, dinitrophenol/anti-dinitrophenol, digoxin/anti-digoxin, and maltose binding protein/anti-maltose binding protein.

7. The device of claim 6 wherein said one part of a specific binding pair of (a) is biotin and said second part of the specific binding pair of (c) is avidin.

8. The device of claim 6 wherein said one part of a specific binding pair of (a) is fluoroscein and said second part of the specific binding pair of (c) s anti-fluoroscein.

9. A method for determining the amount of an analyte in a fluid test sample containing heterophilic antibodies which non-specifically bind to antibodies used to capture and immobilize labeled antibodies and cause a false signal comprising:

(a) applying a test sample to the device of claim 1 and allowing said test sample to flow through said regions (a)–(d);

(b) measuring the amount of the detectable label in regions (b) and (c) of said device; and (c) using the measurements of (b) to calculate the concentration of the analyte in said fluid test sample.

* * * * *